Figure 1:
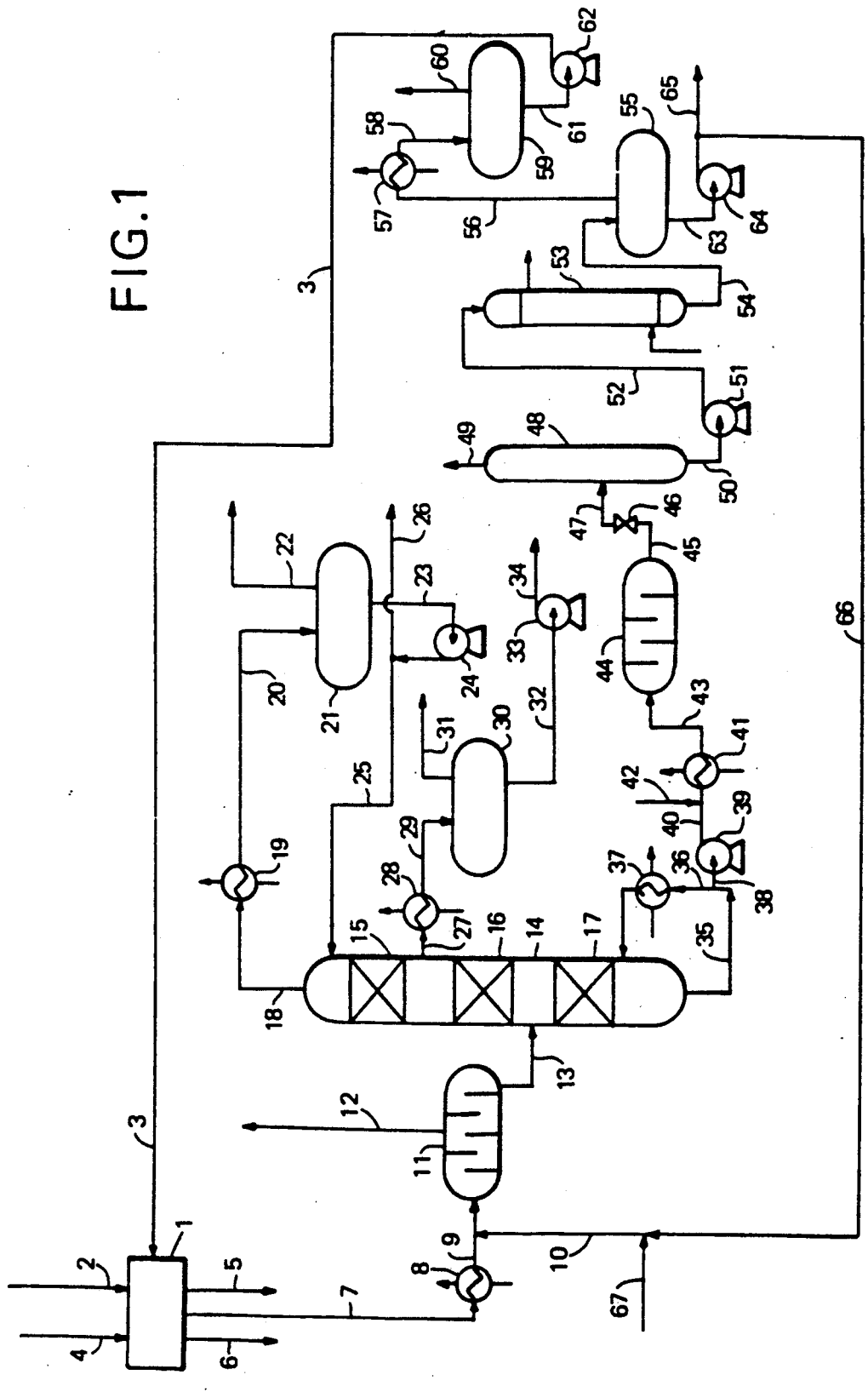

United States Patent [19]
Wilmott et al.

[11] Patent Number: 5,138,106
[45] Date of Patent: Aug. 11, 1992

[54] FATTY ALCOHOLS

[75] Inventors: Martyn Wilmott, Stockton-on-Tees; George E. Harrison, Billericay; John Scarlett, Spennymoor; Michael A. Wood, Middlesbrough; Donald H. McKinley, Radlett, all of England

[73] Assignee: Davy McKee (London) Limited, London, England

[21] Appl. No.: 721,437

[22] PCT Filed: Jan. 16, 1990

[86] PCT No.: PCT/GB90/00065
§ 371 Date: Aug. 12, 1991
§ 102(e) Date: Aug. 12, 1991

[87] PCT Pub. No.: WO90/08123
PCT Pub. Date: Jul. 26, 1990

[30] Foreign Application Priority Data
Jan. 17, 1989 [GB] United Kingdom ............ 8900993

[51] Int. Cl.$^5$ ............ C07C 29/128; C07C 29/149; C07C 29/80; C07C 31/125
[52] U.S. Cl. ............ 568/877; 568/885
[58] Field of Search ............ 568/877, 885

[56] References Cited

U.S. PATENT DOCUMENTS

| | | | |
|---|---|---|---|
| 1,491,076 | 4/1924 | Burghart | 568/877 |
| 3,173,959 | 3/1965 | Rittmeister | 568/885 |
| 3,949,007 | 4/1976 | Grolig et al. | 568/877 |

FOREIGN PATENT DOCUMENTS

| | | | |
|---|---|---|---|
| 188334 | 9/1985 | Japan | 568/877 |
| 7103178 | 9/1971 | Netherlands | 568/877 |
| 734182 | 5/1980 | U.S.S.R. | 568/877 |
| 795573 | 5/1958 | United Kingdom | 568/877 |

Primary Examiner—J. E. Evans
Attorney, Agent, or Firm—Rothwell, Figg, Ernst & Kurz

[57] ABSTRACT

An improved process for refining alcohols produced by hydrogenation of esters wherein the crude hydrogenation product still contains a minor amount of unconverted ester starting material. In one embodiment, the process includes a method for recovering fatty alcohol or alcohols from a fatty alcohol fraction containing a major molar amount of at least one fatty alcohol and a minor molar amount of at least one lower alkyl fatty acid ester. In another embodiment, there is provided a process for the production of fatty alcohols which comprises, in addition to other steps, hydrogenating a lower alkyl fatty acid ester to yield a mixture of a lower alkanol, a fatty alcohol fraction and a minor amount of unreacted lower alkyl fatty acid ester.

12 Claims, 2 Drawing Sheets

FATTY ALCOHOLS

This invention relates to a process for the production of alcohols. More particularly it relates to a process for the production and refining of fatty alcohol products obtained by hydrogenation of esters.

Fatty alcohols, or higher alcohols as they are sometimes designated, are monohydric aliphatic alcohols containing six or more carbon atoms which are derived either from natural sources or are synthesised from petroleum feedstocks. They are often classified by their market usage. As the primary end use of primary alcohols containing between about 6 and about 11 carbon atoms is the production of plasticiser esters, such alcohols are often termed plasticiser alcohols. For higher alcohols containing, for example, from about 11 up to about 20 carbon atoms, the major use is for the production of synthetic detergents; hence such alcohols are often termed detergent alcohols. The distinction between plasticiser alcohols and detergent alcohols is somewhat arbitrary and there is some production of phthalate esters from a $C_{13}$ "oxo" alcohol and also some production of, for example, nonionic surfactants from $C_8$ to $C_{10}$ alcohols.

Although there are some natural products which contain esters which can be hydrogenated to produce alcohols in the plasticiser range, these are more usually produced synthetically from petroleum feedstocks by, for example, the so-called "oxo" process, a process which is also termed oxonation or hydroformylation. Detergent range alcohols, on the other hand, are typically produced by hydrogenation of low molecular alkyl esters of fatty acids Such esters can be produced by transesterification of natural triglycerides or by esterification of the fatty acids obtained by hydrolysis of such triglycerides Examples of triglycerides which can be used as raw materials include natural oils, such as coconut oil, rape seed oil, and palm oils, and animal fats, such as lard, tallow, and fish oil. As such natural raw materials usually contain mixtures of triglycerides, the alcohol products obtained upon hydrogenation are also mixtures of n-alkanols of differing molecular weight. Such mixtures of alkanols are acceptable for production of detergents without prior separation of the alkanols one from another.

Whatever the commercial end use of the fatty alcohol or fatty alcohol mixture the user generally insists that the alcohol product must have as low an acid value as possible and also as low a saponification value as possible. The acid value (AV) is a measure of the free acid content of the alcohol product and is defined as the number of mg of KOH required to neutralise the free fatty acid in 1 g of alcohol. The saponification value (SV) gives, together with the acid value, a measure of the free ester content of the alcohol product and is defined as the number of mg of KOH required to saponify the esters and acids in 1 g of alcohol. The ester value (EV) is the number obtained by subtracting the acid value from the saponification value (EV = SV − AV). In all cases the lower the value is (AV, SV, or EV), the better is considered to be the quality of the alcohol product. Another measure of purity of saturated alcohols is the iodine value (IV), i.e. the number of g of $I_2$ absorbed by 100 g of the alcohol The iodine value indicates the ethylenic double bond content of the alcohol product. Again, it is generally considered desirable to have as low an iodine value as possible for a saturated alcohol Examples of commercial fatty alcohol products are the products sold under the following trade names:

| Descriptive Name | Trade Mark | Derived from | Approx. composition, wt %, 100% alcohol basis | | | | |
|---|---|---|---|---|---|---|---|
| | | | $C_{12}$ | $C_{14}$ | $C_{16}$ | $C_{18}$ | $C_{20}$ |
| dodecanol | CO-1214 | coconut | 67 | 26 | 7 | | |
| | Dehydag | coconut | 72 | 27 | 1 | | |
| tetradecanol-octadecanol | CO-1418 | coconut | 12 | 43 | 22 | 23 | |
| hexadecenol | CO-1695 | coconut | | 1 | 96 | 3 | |
| hexadecanol-octadecanol | TA-1618 | tallow | | 4 | 28 | 67[a] | 1 |
| octadecenol | CO-1895 | coconut | | | 2 | 97 | 1 |
| octadecenol | Dehydag HD | natural oils | | | 4 | 94[b] | 2 |
| octadecenol-octadecanol | Dehydag 60/65 | natural oils | 1 | 4 | 26 | 68[b] | ·1 |

Notes:
[a] = includes 1% $C_{17}$ alcohol
[b] = octadecenol

The esters usually used as raw materials for the production of detergent range alcohols are the methyl esters. A problem arises in refining of the product alcohol mixtures because the boiling point of one or more of the methyl esters present in the ester mixture which is hydrogenated will usually be close to that of one of the product alcohols. Hence it becomes difficult, if not impossible, to separate by distillation any unconverted methyl esters from the product alcohol mixture.

As an illustration of the difficulty of separating fatty alcohols from methyl fatty acid esters, particularly from mixtures containing a major amount of a mixture of fatty alcohols and a minor amount of a mixture of methyl fatty acid esters, reference may be made to the following list of boiling points:

| Substance | Boiling point | Pressure mm Hg (bar) |
|---|---|---|
| 1-dodecanol | 150° C. | 20 (0.027) |
| methyl laurate | 149° C. | 20 (0.027) |
| 1-tetradecanol | 167° C. | 15 (0.020) |
| methyl myristate | 170° C. | 15 (0.020) |
| 1-hexadecanol | 189.5° C. | 15 (0.020) |
| methyl palmitate | 192° C. | 15 (0.020) |
| 1-octadecanol | 210° C. | 15 (0.020) |
| methyl stearate | 213° C. | 15 (0.020) |

A mixture containing all of these components, such as might be produced by hydrogenation of a mixture of methyl esters of $C_{12}$- to $C_{18}$-fatty acids produced by hydrolysis of a natural triglyceride, is difficult (if not impossible) to separate satisfactorily by distillation without recourse to use of multiple distillation columns.

To avoid the expense of multiple distillation columns, one of two approaches is normally adopted. The first approach involves use of somewhat vigorous hydrogenation conditions, including use of high pressures and temperatures so as to ensure that as small a proportion of unconverted methyl esters remains in the hydrogenation product. Although this largely obviates the problem of separating the methyl esters from the product alcohols, the use of vigorous hydrogenation conditions has drawbacks, particularly in that such conditions also tend to increase the yield of alkane and ether byproducts which represent a significant loss of potentially valuable alcohols. In addition catalyst consumption is rather high and the use of high pressure equipment increases the capital and running costs of the plant.

The second approach to the problems associated with the presence of unconverted esters in the alcohol hydrogenation product is to use less vigorous hydrogenation conditions, which reduces the loss of alcohol product by formation of alkane and ether byproducts, with subsequent removal of the unconverted ester by hydrolysis with hot aqueous alkali, such as hot sodium hydroxide solution. In this case the remaining ester is converted to a fatty acid salt which is lost in the aqueous phase. In addition this procedure involves consumption of sodium hydroxide or other alkali. Finally, as the sodium or other alkali metal salts of the fatty acids act as soaps, problems may arise in separating the aqueous phase from the alcohol product due to formation of emulsions.

For further background information about the production of fatty alcohols reference may be had to the following reviews:
1. "Fatty alcohols", by J.A. Monick, J. Am. Oil Chemists' Soc., November 1979, Vol. 56, pages 853A to 860A;
2. "Natural fats and oils route to fatty alcohols", by Henning Buchold, Chemical Engineering, February 21, 1985, pages 42 and 43;
3. "Manufacture of Fatty Alcohols Based on Natural Fats and Oils", by Udo R. Kreutzer, JAOCS, Vol 61, No. 2 (February 1984), pages 343 to 348;
4. "production of Fatty Alcohols from Fatty Acids", by Theodor Voeste and Henning Buchold, JAOCS, Vol. 61, No. 2 (February 1984), pages 350 to 352;
5. "Alcohols, higher aliphatic", Kirk-Othmer Encyclopedia of Chemical Technology, Third Edition (1978), Vol. 1, (published by J. Wiley & Sons. Inc., New York), pages 716 to 739; and
6. "Technical Processes for the Manufacture of Fatty Alcohols" by H.-D. Kompp and H.P. Kubersky, in "Fatty Alcohols - Raw Materials, Methods, Uses" published in 1982 by Henkel KGaA, Dusseldorf, at pages 49 to 74.

It would be desirable to provide a method enabling fatty alcohol products obtained by hydrogenation of esters to be purified by distillation, even though such products contain appreciable proportions of unconverted esters. The existence of such a method would enable hydrogenation of the ester feedstock to be carried out under relatively mild conditions with less formation of byproduct alkane and hence with higher yields of alcohol products than can be obtained by conventional methods of manufacture of fatty alcohols by this route.

The present invention accordingly seeks to provide an improved process for refining alcohols produced by hydrogenation of esters, such as methyl esters produced by transesterification of natural glycerides or by esterification of fatty acids produced by hydrolysis of such triglycerides, wherein the crude hydrogenation product still contains a minor amount of unconverted ester starting material. It further seeks to provide an improved process for production of fatty alcohols from fatty alcohol fractions obtained by hydrogenation of low molecular alkyl esters, especially methyl esters, of fatty acids derived from natural triglycerides, under conditions which minimise formation of byproduct alkanes and ethers followed by refining of the resulting ester containing hydrogenation product.

According to the present invention there is provided a process for the recovery of a fatty alcohol or alcohols from a fatty alcohol fraction containing a major molar amount of at least one fatty alcohol and a minor molar amount of at least one lower alkyl fatty acid ester, which process comprises:

(a) subjecting the fatty alcohol fraction to transesterification in the presence of a transesterification catalyst in a first transesterification zone maintained under transesterification conditions, thereby to convert substantially all of any lower alkyl fatty acid ester present in the feed mixture by ester interchange with a corresponding amount of fatty alcohol or alcohols to lower alkanol and to a wax ester derived from a fatty alcohol and a fatty acid;

(b) separating resulting lower alkanol from the reaction mixture of step (a) by vaporisation to yield an intermediate transesterification product mixture that is at least partially free from lower alkanol and contains a fatty alcohol or alcohols and a wax ester or esters;

(c) distilling fatty alcohol or fatty alcohols and wax ester or wax esters of the intermediate transesterification product mixture of step (b) to yield (i) an overhead fraction that contains the fatty alcohol or alcohols and is substantially free from lower alkyl fatty acid ester, and (ii) a distillation residue comprising fatty alcohol or alcohols, and wax ester or esters;

(d) subjecting the distillation residue of step (c) to transesterification in the presence of added lower alkanol and of a transesterification catalyst in a second transesterification zone maintained under transesterification conditions, thereby to reconvert wax ester or esters to lower alkyl fatty acid ester or esters and to fatty alcohol or alcohols;

(e) evaporating unreacted lower alkanol from the reaction mixture of step (d) to yield a liquid residue that is substantially free from lower alkanol; and (f) distilling fatty alcohol or alcohols and lower alkyl fatty acid ester or esters of the liquid residue of step (e) to produce (i) an overhead product containing a mixture of a lower alkyl fatty acid ester or esters and fatty alcohol or alcohols and (ii) a relatively involatile residue.

In another aspect the invention provides a process for the production of fatty alcohols which comprises hydrogenating a lower alkyl fatty acid ester or esters in a hydrogenation zone containing a charge of a hydrogenation catalyst and maintained under hydrogenation conditions to yield a mixture of (i) lower alkanol and (ii) a fatty alcohol fraction containing a fatty alcohol or alcohols and a minor amount of unreacted lower alkyl fatty acid ester or esters; and which further comprises:

(a) subjecting the fatty alcohol fraction to transesterification in the presence of a transesterification catalyst in a first transesterification zone maintained under transesterification conditions, thereby to convert substantially all of any lower alkyl fatty acid ester present in the feed mixture by ester interchange with a corresponding amount of fatty alcohol or alcohols to lower alkanol and to a wax ester derived from a fatty alcohol and a fatty acid;

(b) separating resulting lower alkanol from the reaction mixture of step (a) by vaporisation to yield an intermediate transesterification product mixture that is at least partially free from lower alkanol and contains a fatty alcohol or alcohols and a wax ester or esters;

(c) distilling fatty alcohol or fatty alcohols and wax ester or wax esters of the intermediate transesterification product mixture of step (b) to yield (i) an overhead fraction that contains the fatty alcohol or alcohols and is substantially free from lower alkyl fatty acid ester, and (ii) a distillation residue comprising fatty alcohol or alcohols, and wax ester or esters;

(d) subjecting the distillation residue of step (c) to transesterification in the presence of added lower alkanol and of a transesterification catalyst in a second transesterification zone maintained under transesterification conditions, thereby to reconvert wax ester or esters to lower alkyl fatty acid ester or esters and to fatty alcohol or alcohols;

(e) evaporating unreacted lower alkanol from the reaction mixture of step (d) to yield a liquid residue that is substantially free from lower alkanol;

(f) distilling fatty alcohol or alcohols and lower alkyl fatty acid ester or esters of the liquid residue of step (e) to produce (i) an overhead product containing a mixture of a lower alkyl fatty acid ester or esters and fatty alcohol or alcohols and (ii) a relatively involatile residue; and (g) recycling material of the overhead product of step (f) to the hydrogenation step.

In this specification the term "fatty alcohol" means an alkanol, preferably a linear alkanol, containing from about 6 to about 26 carbon atoms. Preferred fatty alcohols contain from about 10 to about 20 carbon atoms. Typical fatty alcohols include 1-decanol, 1-dodecanol, 1tetradecanol, 1-hexadecanol, 1-octadecanol, 1-octadecenol and the like, and mixtures thereof. The term "lower alkyl" means $C_1$- to $C_4$-alkyl, including methyl, ethyl, n-propyl, iso-propyl, n-butyl, iso-butyl and sec-butyl. The preferred lower alkyl radical is methyl. Similarly the term "lower alkanol" embraces $C_1$ to $C_4$ alkanols, including methanol, ethanol, n-propanol, iso-propanol, n-butanol, iso-butanol, and sec-butanol. Methanol is the preferred lower alkanol. By the term "fatty acids" we mean alkyl or alkenyl carboxylic acids, preferably linear alkyl or alkenyl carboxylic acids, containing from about 6 to about 26 carbon atoms, preferably about 10 to about 20 carbon atoms. Examples of such fatty acids are decanoic acid (capric acid), dodecanoic acid (lauric acid), tetradecanoic acid (myristic acid), pentadecanoic acid, hexadecanoic acid (palmitic acid), heptadecanoic acid (margaric acid), octadecanoic acid (stearic acid or isostearic acid), octadecenoic acids (oleic acid, linoleic acid or linolenic acid), eicosanoic acid (arachidic acid) and docosanoic acid (behenic acid). Mixtures of fatty acids are of especial importance as raw materials from which the lower alkyl fatty acid esters used as starting material in the hydrogenation step are prepared. Such mixtures of acids can be obtained by hydrolysis of naturally occurring triglycerides such as coconut oil, rape seed oil, palm oils, tallow, lard and fish oil. If desired, such mixtures of acids can be subjected to distillation to remove lower boiling acids having a lower boiling point than a chosen temperature and thus produce a "topped" mixture of acids, to remove higher boiling acids having a boiling point higher than a second chosen temperature and thus produce a "tailed" mixture of acids, or to remove both lower and higher boiling acids and thus produce a "topped and tailed" mixture of acids.

In the hydrogenation of lower alkyl fatty acid esters there can be used vapour phase hydrogenation conditions in which the composition of the gas stream is selected so that at all times the material in contact with the hydrogenation catalyst is above the dew point, preferably at least about 5° C. above the dew point. Suitable hydrogenation catalysts include known ester hydrogenation catalysts such as reduced copper oxide-zinc oxide (see GB-B-2116552), and copper chromite, and promoted copper chromite catalysts. The preferred catalysts are reduced copper oxide-zinc oxide catalysts of the type disclosed in GB-B-2116552. The preferred copper chromite catalysts are those containing from about 25 to about 45 percent by weight of copper and from about 20 to about 35 percent by weight of chromium, calculated as metal. Typical hydrogenation conditions include use of temperatures of up to about 260° C., such as temperatures in the range of from about 140° C. to about 240° C., and pressures in the range of from about 5 bar to about 100 bar Liquid phase hydrogenation conditions can alternatively be used, if desired, for production of a fatty alcohol fraction by hydrogenation of a lower alkyl fatty acid ester or esters. In liquid phase hydrogenation typical operating conditions include use of a temperature of from about 180° C. to about 300° C. and a pressure of from about 50 bar to about 300 bar.

The hydrogenation mixture obtained by hydrogenating a lower alkyl fatty acid ester or mixture of esters contains, in addition to a fatty alcohol or fatty alcohol mixture, also lower alkanol, such as methanol. The methanol or other lower alkanol is separated in any known manner, as by distillation in one or more stages, from the fatty alcohol or alcohols to yield a fatty alcohol fraction suitable for use in the process of the invention. Such a fatty alcohol fraction typically contains, besides possibly a minor molar amount of methanol or other lower alkanol (usually less than about 5 mole %), a major molar amount of a fatty alcohol or alcohols (usually about 90 mole % or more) and a minor molar amount of unreacted lower alkyl fatty acid ester or esters (usually less than about 5 mole %).

In transesterification step (a) the fatty alcohol fraction is subjected to transesterification in the presence of a transesterification catalyst. Any known transesterification catalyst may be used Examples include alkyl titanates, alkali metal alkoxides, and metallic tin and stannous hydroxide. Although acids, such as sulphuric acid and sulphonic acids, have been proposed as liquid phase transesterification catalysts in the prior art, the use of such catalysts is best avoided since there is a risk of the fatty alcohol product becoming contaminated with sulphurous impurities. Other transesterification catalyst systems which have been proposed, but are not preferred, include bases, compounds of alkali and alkaline earth metals, water and metals such as zinc, cadmium, lead and their compounds. It is also contemplated that acidic resins containing, for example, —SO₃H and/or —COOH groups or basic resins containing, for example, basic substituted ammonium groups can be used as transesterification catalysts.

A particularly preferred class of transesterification catalyst is the alkyl titanates. Any alkyl titanate may be added as catalyst but, as the alkyl titanate will itself participate in ester interchange, the alkoxide radicals originally present in the alkyl titanate will tend to undergo exchange with alkoxide radicals derived from the fatty alcohol or alcohols during the operation of the process of the invention.

Another particularly preferred class of transesterification catalyst is the alkali metal alkoxides, such as sodium methoxide or sodium ethoxide. Again exchange of alkoxide radicals in the catalyst with alkoxide radicals derived from the fatty alcohol or alcohols will tend to occur with time in the first transesterification zone. Alternatively there may be used an alkali metal alkoxide derived from the fatty alcohol product itself, or from one or more of them if a mixture of fatty alcohols is to be produced.

The transesterification conditions used in step (a) will to a large extent depend upon the activity of the transesterification catalyst. Although the use of elevated pressures is not ruled out, it will normally be preferred to operate at a substantially atmospheric pressure or below, for example a pressure in the range of from about 0.1 bar to about 1.2 bar. In this way the vaporisation of methanol or other lower alkanol of step (b) is facilitated during the course of the transesterification reaction of step (a). Removal of the lower alkanol during transesterification drives the transesterification reaction towards completion.

When using an alkyl titanate a temperature of up to about 240° C., such as a temperature in the range of from about 120° C. to about 200° C., is typically used, for example a temperature of from about 170° C. to about 180° C. Alkali metal alkoxides enable use of lower operating temperatures, e.g. in the range of from about 40° C. to about 100° C., but normally require introduction of extra processing steps as will be further explained below.

Similar transesterification catalysts and temperature conditions can be used in step (d). However, it will usually be preferred to employ in step (d) a superatmospheric pressure, for example a pressure of from about 1.5 bar to about 50 bar, in order to maintain the lower alkanol (e.g. methanol) in the liquid phase in the second transesterification zone.

As already mentioned steps (a) and (b) are preferably conducted simultaneously in a first transesterification zone that has provision for recovery overhead of the liberated lower alkanol.

An advantage of the use of an alkyl titanate as transesterification catalyst is that the subsequent distillation and/or evaporation steps (i.e. step (c) and steps (e) and (f)) can be conducted without prior removal of the catalyst. However, when using an alkali metal alkoxide as transesterification catalyst, it is preferable to neutralise the catalyst prior to distillation and/or evaporation. Conveniently this neutralisation step can be effected by passing the catalyst containing material through a bed of an ion exchange resin containing —SO₃H and/or —COOH groups, thus removing the alkali metal from the liquid mixture:

where R represents the resin and —OR' represents an alkoxids radical.

A further advantage of the use of alkyl titanates is that the catalyst remaining in the relatively involatile residue of step (f) can be used to form at least a part of the transesterification catalyst used in step (a). The balance of any amount of catalyst required can then be supplied by make up alkyl titanate. Control of "heavies" in the process can be achieved by purging a part of the relatively involatile residue of step (f); the remainder of this relatively involatile residue can be recycled for use in step (a).

When using an alkali metal hydroxide as transesterification catalyst, on the other hand, there will usually be no residual catalyst in the relatively involatile residue of step (f) as neutralisation will usually be practised prior to any distillation step. Similarly, if a resin catalyst is used as a transesterification catalyst, there will be no catalyst dissolved in the relatively involatile residue of step (f). Hence recycle of the relatively involatile residue has no benefit in these cases and the relatively involatile residue of step (f) can be purged from the plant and used as fuel.

If an alkyl titanate transesterification catalyst is used, steps (e) and (f) can be carried out without prior removal of the catalyst. In this case it is best to operate with as short residence times as possible in these steps so as to minimise the risk of substantial reversion of the transesterification reaction with consequent re-formation of wax esters in these steps. Hence it is preferred to effect step (e) by flash distillation so as to minimise the residence time in this step and to effect step (f), for similar reasons, in a falling film or wiped film evaporator.

Distillation steps (c) and (f) are normally effected at or near atmospheric pressure or below, for example at a pressure in the range of from about 0.005 bar to about 1.2 bar.

In order that the invention may be clearly understood and readily carried into effect two preferred forms of alcohol production plant designed to operate according to the teaching of the present invention will now be described, by way of example only, with reference to the accompanying drawings FIGS. 1 and 2 of which are each a flow diagram of a respective plant.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may additionally be required in a commercial plant. The provision of such ancillary item, of equipment forms no part of the present invention and is in accordance with conventional chemical engineering practice.

Referring to FIG. 1, a hydrogenation plant 1 is supplied in line 2 with a feed ester stream, in line 3 with recycled material, and in line 4 with a hydrogen stream. The feed ester stream in line 1 is a mixture of methyl esters obtained by esterification of a fatty acid mixture obtained by hydrolysis of coconut oil, followed by "topping and tailing". This fatty acid mixture contains approximately 65 mole % dodecanoic acid, 25 mole % tetradecanoic acid and 10 mole % hexadecanoic acid.

Hydrogenation plant 1 can operate using any suitable ester hydrogenation process and with any suitable ester hydrogenation catalyst. A reduced copper oxide-zinc oxide catalyst of the type disclosed in GB-B-2116552 is an example of a suitable hydrogenation catalyst. Plant 1 may include one or more hydrogenation stages, as well as a preliminary distillation zone for separating at least a major part of the by-product methanol The hydrogen stream in line 2 is produced in conventional manner from synthesis gas followed by a water gas shift reaction, $CO_2$ removal and, if desired, further purification by pressure swing absorption. It may contain one or more inert gases, such as nitrogen, methane and argon. The byproduct methanol can be recycled for production of further methyl esters in line 5. A purge gas stream is taken from hydrogenation plant 1 in line 6. Hydrogenation plant 1 can operate using a vapour phase regime in which the reaction mixture in contact with the catalyst is always above its dew point. Alternatively it may be operated using a liquid phase regime, in which case a copper chromite catalyst will usually be preferred.

A crude fatty alcohol stream is recovered from plant 1 in line 7. This contains a minor amount of unconverted methyl esters, besides minor amounts of byproduct alkanes, unknowns and "heavies". The crude fatty alcohol stream passes through heat exchanger 8 in which its temperature is adjusted to about 160° C. to about 200° C., preferably about 170° C. to about 190° C., e.g. 190° C. The hot stream in line 9 is admixed with a mixture of fresh and recycled ester interchange catalyst (transesterification catalyst), e.g. an alkyl titanate, supplied in line 10 and passes into a first ester interchange reactor 11 which provides a first transesterification zone. Reactor 11 is designed so as to provide a residence time therein in the range of from about 10 minutes up to about 120 minutes, preferably from about 15 minutes to about 60 minutes. The length of the residence time depends upon the temperature of the stream in line 9 and in reactor 11, as well as the effective concentration of the alkyl titanate supplied in line 10. In reactor 11 the methyl esters of the fatty acids present in the feed stream in line 7 are converted to wax esters, i.e. fatty alcohol esters of the acid moieties of the methyl esters, by transesterification of the methyl esters with product fatty alcohols. Most of the methanol formed by transesterification is recovered as a vapour in line 12 from the vapour space in vessel 11 and can be condensed and recycled to the methyl ester production plant (not shown).

The product from the first ester interchange reactor 11 contains, besides a major molar amount of product alcohols, also minor molar amounts of alkane by-products, wax esters and "heavies", as well as traces of methanol. It is passed via line 13 into a product column 14 which is provided with three beds of structured packing 15, 16 and 17. Light ends, consisting mainly of alkane by-products, as well as traces of methanol, are recovered overhead in line 18 and are condensed by means of condenser 19. The resulting condensate in line 20 accumulates in reflux drum 21 which is vented to a vacuum pump (not shown) operating at 0.005 bar by line 22. Some alkanes are returned to product column 13 via line 23, pump 24 and line 25 to provide a reflux stream, whilst the net production of alkanes passes via line 26 to storage.

Product alcohols are withdrawn as vapour from product column 14 in line 27 and are condensed by means of condenser 28. The condensate passes on in line 29 to product drum 30 which is vented to a vacuum unit (not shown) by line 31. Liquid product alcohols are passed via line 32, pump 33 and line 34 to product storage.

Bottoms product is withdrawn from product column 14 in line 35 and passed via line 36 to a falling film reboiler 37 which is operated at a temperature in the range of from about 210° C. to about 245° C., e.g. 240° C. Part of the bottoms product is withdrawn in line 38 and is pumped by pump 39 via line 40 to heat exchanger 41. Prior to entry to heat exchanger 41 excess methanol from line 42 is admixed with this part of the bottoms product. The quantity of methanol admixed via line 42 is typically at least about 5 times the stoichiometric quantity equivalent to the wax esters present in the bottom product up to about 100 times this stoichiometric quantity, for example about 80 times the stoichiometric quantity In this way the equilibrium between wax esters and methanol, on the one hand, and methyl fatty acid esters, fatty alcohol and excess methanol, on the other hand, is shifted away from wax ester formation towards methyl fatty acid ester formation.

In heat exchanger 41 the temperature of the mixture of methanol and bottoms product, which still contains alkyl titanate transesterification catalyst, is adjusted. The mixture passes on via line 43 to a second ester interchange reactor 44 which provides a second transesterification zone and is designed to provide a residence time of from about 30 minutes to about 240 minutes, preferably from about 60 minutes to about 180 minutes, e.g. about 120 minutes. The temperature in reactor 44 lies in the range of from about 160° C. to about 195° C. e.g. about 180° C. The size, and hence the residence time, selected for reactor 44 should be sufficient to allow the ester interchange to proceed to equilibrium at the temperature selected. The pressure in reactor 44 is typically about 42 bar. From second ester interchange reactor 44 the resulting transesterification product mixture is fed via line 45 through a pressure let down valve 46 to reduce its pressure to about 1.3 bar It then continues in line 47 to a heated flash vessel 48. Methanol vapour is recovered overhead in line 49 and is condensed by means of a condenser (not shown) for reuse elsewhere in the plant or for manufacture of further methyl esters.

The residual liquid phase exits flash column 48 in line 50 and is pumped by pump 51 through line 52 via a pressure let down valve (not shown) to falling film evaporator 53 which is operated at a maximum temperature of about 240° C. and at a pressure of about 0.005 bar. A mixture of vapour and liquid exits falling film evaporator 53 in line 54 and passes into separation drum 55. The vapour is recovered in line 56 and condensed by condenser 57. The resulting condensate is passed in line 58 to drum 59 which is connected to a vacuum system (not shown) by line 60. The liquid condensate, which comprises a mixture of product fatty alcohols, methyl esters, some methanol and traces of by-products, is recovered in line 61 and pumped by pump 62 to form the recycle stream in line 3.

The liquid from drum 55 is passed by line 63 and pump 64 either for waste disposal via line 65 or for recycle via line 66 to line 10.

Fresh alkyl titanate transesterification catalyst can be added as required via line 67.

The approximate flow rates of various of the streams expressed in molar units are summarised in Table 1 below:

TABLE 1

| Line | 2 | 3 | 7 | 13 | 26 | 34 | 38 | 42 | 45 | 49 | 63 |
|---|---|---|---|---|---|---|---|---|---|---|---|
| Methyl esters | 100.8 | 1.8 | 2.0 | trace | — | trace | — | — | 1.8 | — | — |
| Fatty alcohols | 9.7 | 9.7 | 107.0 | 105.0 | 0.2 | 96.6 | 8.0 | — | 9.8 | — | 0.1 |
| Fatty acids | 0.5 | — | — | — | — | — | — | — | — | — | — |
| Alkanes | — | — | 2.0 | — | — | — | 2.0 | — | — | — | — |
| Wax esters | — | — | — | 2.0 | — | — | 2.0 | — | 0.2 | — | 0.2 |
| Unknowns | 0.5 | — | 0.5 | 0.5 | — | 0.5 | — | — | — | — | — |
| "Heavies" | — | — | — | — | — | — | 0.2 | — | 0.2 | — | 0.2 |
| Methanol | 27.0 | — | — | trace | — | — | — | 80 | 78.2 | 77.9 | — |
| Water | 0.1 | — | — | — | — | — | — | — | — | — | — |

Figure 2:
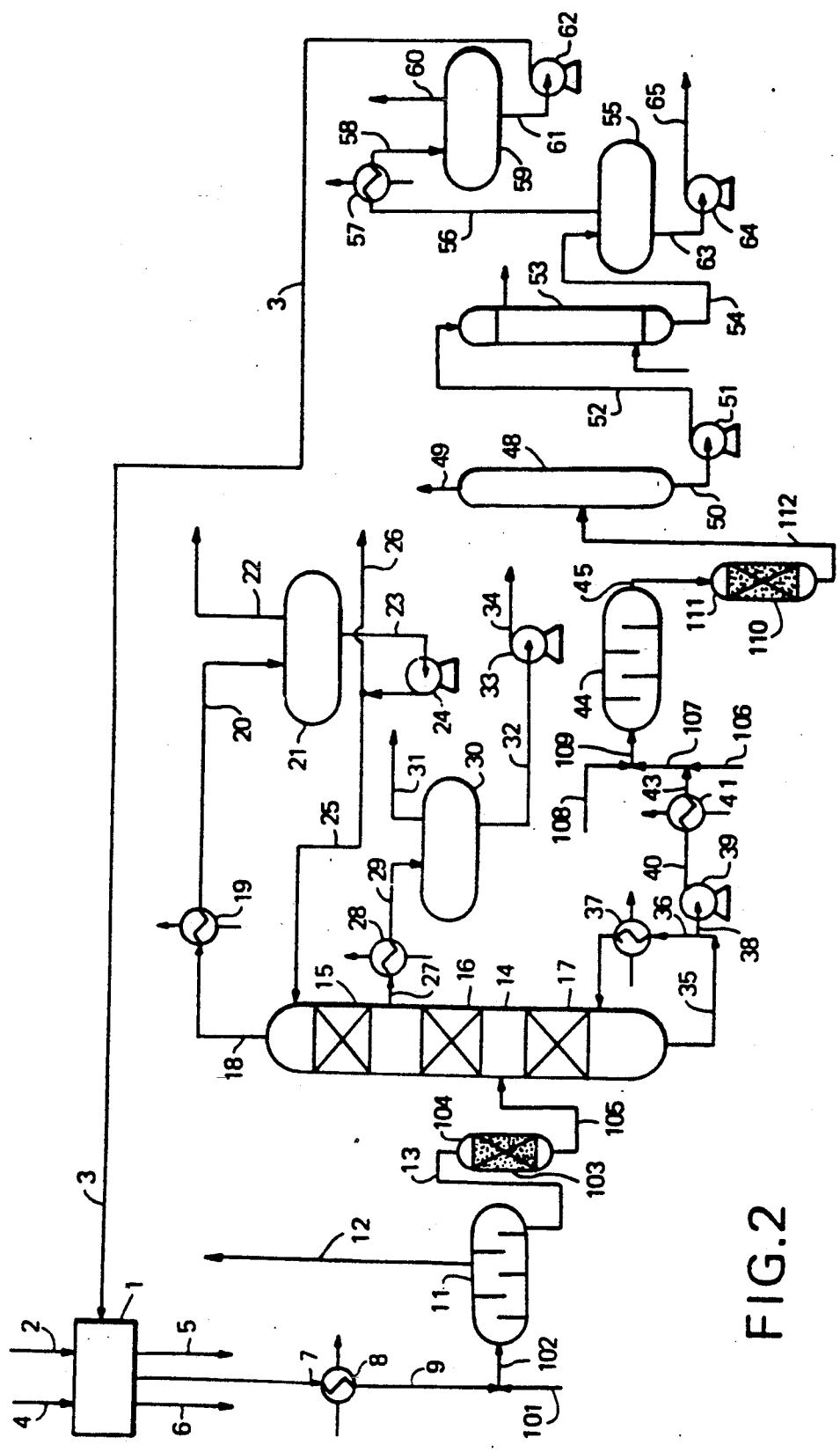

FIG. 2 illustrates a modified form of the plant of FIG. 1 which is designed to operate using an alkali metal alkoxide as the transesterification catalyst in place of an alkyl titanate. In FIG. 2 like reference numerals have been used to indicate similar parts to those illustrated in FIG. 1.

The temperature of the crude fatty alcohol stream in line 7 is adjusted to 45° C. in heat exchanger 8. A solution containing 10% w/v of sodium methoxide in dry methanol is added in line 101 so as to provide a concentration of 0.05% w/v of sodium methoxide in the material flowing in line 102. In this plant first ester interchange reactor 11 is designed to provide, typically, a residence time therein of about 30 minutes. The material exiting reactor 11 in line 13 is then passed through a bed 103 of ion exchange resin in vessel 104 to neutralise the catalyst. The ion exchange resin of bed 103 can contain sulphonic acid and/or carboxylic acid groups. The catalyst free stream passes on in line 105 to product column 14.

Removal of the sodium methoxide catalyst prior to distillation in product column 14 is desirable so as to obviate the formation of condensation by-products and dark coloured organic tars, which would be promoted by the presence of sodium methoxide in the mixture at the elevated temperatures prevailing in the product column 14.

Recovery of product alcohol in product column 14 is effected in the same way as for the plant of FIG. 1. The bottom product in lines 35, 38 and 40 is then cooled to about 50° C. in heat exchanger 41. A similar stoichiometric excess of methanol is added from line 106 to the liquid stream in line 43. The resulting mixture in line 107 is then admixed with a 10% w/v solution of sodium methoxide in dry methanol supplied by way of line 108 at a rate sufficient to provide a concentration of about 0.05% w/v sodium methoxide in the mixed stream in line 109 before entry to second ester interchange reactor 44 which is designed for a residence time of about 120 minutes. The interchanged product stream in line 45 is then passed through a second bed 110 of ion exchange resin, which contains, for example, sulphonic acid groups and/or carboxylic acid groups, in vessel 111. This removes sodium ions from the liquid phase and neutralises the sodium methoxide transesterification catalyst. The neutralised liquid phase passes on in line 112 to flash column 48.

As the material in line 112 contains no transesterification catalyst there is no need to recycle "heavies" via line 66 (as in the plant of FIG. 1). Moreover, as there is no catalyst remaining in the material in line 112, the risk of reversion of methyl esters to wax esters and loss of methanol vapour in columns 48 and 53 by ester interchange with fatty alcohols product is obviated.

In a modification of the plant of FIG. 2 columns 48 and 53 are replaced by a batch still (not shown). In this case the material in line 112 is collected until there is sufficient to justify operating the batch still.

The invention is further illustrated in the following Examples.

EXAMPLE 1

A crude fatty alcohol product containing a minor amount of unconverted fatty acid methyl esters was prepared by hydrogenating in a laboratory hydrogenation reactor under vapour phase conditions (i.e. under conditions such that the reaction mixture in contact with the catalyst was at all times above its dew point) a mixture of fatty acid methyl esters obtained from a "topped and tailed" fatty acid mixture produced by hydrolysis of coconut oil. The catalyst used was a reduced copper oxide-zinc oxide ester hydrogenation catalyst Prior to use the crude alcohol product mixture was distilled to remove substantially all the methanol produced as coproduct in the hydrogenation step.

Three samples of the substantially methanol free crude fatty alcohol product were each heated to 200° C. under a nitrogen atmosphere for 30 minutes at 0 99 bar with 0.03% w/w of Tilcom BIP (trade mark of Tioxide Chemical Division of British Titan Products) This material is reported to be a mixed isopropyl/butyl titanate. Subsequent analysis showed that, in the presence of a large excess of fatty alcohols and under conditions allowing methanol to escape from the reaction system, substantially all of the methyl esters had been transformed into wax esters. The results are plotted in Table 2 below which indicates the amounts of the components present in % w/w In Table 2 "$C_{12}$ Me ester" means methyl dodecanoate, whilst "$C_{14}$ Me ester", "$C_{16}$ Me ester", and "Me ester" represent respectively the corresponding methyl esters of the $C_{14}$, $C_{16}$ and $C_{18}$ carboxylic acids. There were detected sixteen unidentified compounds, listed as "Unknowns 1 to 16" in Table 2, in minor or trace amounts.

TABLE 2

| COMPONENT | FEED | PRODUCT | | |
|---|---|---|---|---|
| | | Run 1 | Run 2 | Run 3 |
| Methanol | 2.19 | 0.03 | 0.11 | 0.02 |
| $C_{12}$ Alkane | 0.34 | 0.27 | 0.20 | 0.24 |
| $C_{14}$ Alkane | 0.37 | 0.37 | 0.34 | 0.34 |
| $C_{16}$ Alkane | 0.31 | 0.35 | 0.33 | 0.33 |
| Unknown Compounds 1 to 6 | 1.34 | 1.68 | 1.75 | 1.90 |
| ($C_{12}$ Me Ester +) | 1.79* | 0.06 | 0.10 | 0.04 |
| $C_{18}$ Alkane) | | 0.04 | 0.03 | 0.03 |
| Unknowns 7 + 8 | 0.16 | 0.3 | 0.49 | 0.33 |
| Unknowns 9 + 10 | 0.87 | trace | trace | trace |
| $C_{12}$ Alcohol | 57.30 | 56.97 | 55.86 | 54.33 |
| $C_{14}$ Me Ester | 0.21 | trace | trace | trace |
| Unknowns 11 to 13 | 0.17 | 0.17 | 0.14 | 0.23 |
| $C_{14}$ Alcohol | 24.64 | 24.86 | 24.94 | 26.52 |
| $C_{16}$ Me Ester | 0.09 | trace | trace | trace |
| Unknowns 14 + 15 | 0.14 | 0.03 | 0.03 | 0.08 |
| $C_{16}$ Alcohol | 9.45 | 9.42 | 9.66 | 9.47 |

TABLE 2-continued

| COMPONENT | FEED | PRODUCT | | |
|---|---|---|---|---|
| | | Run 1 | Run 2 | Run 3 |
| $C_{18}$ Me Ester | 0.23 | 0.02 | 0.03 | 0.03 |
| Unknown 16 | 0.05 | trace | trace | trace |
| $C_{18}$ Alcohol | 0.35 | 0.45 | 0.50 | 0.46 |
| Wax Esters: | | | | |
| (a) $C_{12}$—$C_{12}$ | — | 2.78 | 2.60 | 3.20 |
| (b) $C_{12}$–$C_{14}$ | — | 1.42 | 1.72 | 1.68 |
| (c) $C_{12}$–$C_{16}$ | — | 0.75 | 0.80 | 0.67 |
| (d) $C_{14}$—$C_{14}$ | — | trace | trace | 0.08 |

*Components not resolved.

In Table 2 the wax esters are identified variously as (a) $C_{12}$–$C_{12}$, (b) $C_{12}$–$C_{14}$, (c) $C_{12}$–$C_{16}$ and (d) $C_{14}$ $C_{14}$–$C_{14}$. These materials are thought, by reason of their gas chromatographic retention times, to represent respectively:

(a) the ester of a $C_{12}$ alkanol with a $C_{12}$ fatty acid;

(b) mixture of esters of a $C_{12}$ alkanol with a $C_{14}$ fatty acid and of a $C_{14}$ alkanol with a $C_{12}$ fatty acid;

(c) mixture of esters of a $C_{12}$ alkanol with a $C_{16}$ fatty acid and of a $C_{16}$ alkanol with a $C_{12}$ fatty acid; and (d) the ester of a $C_{14}$ alkanol with a $C_{14}$ fatty acid.

The results plotted in Table 2 were obtained using a Pye Unicam 4500 Gas Chromatograph fitted with 25 metre long Nordian NB351 FAME capillary column and with a flame ionisation detector. The carrier gas was helium at a column inlet pressure of 2.39 bar The sample injection volume was 0.4 microlitres. The column was temperature programmed as as follows: 2 minutes at 80° C. after sample injection, followed by heating at 8° C. per minute to 230° C., whereafter the temperature was maintained at this value. The injection port temperature was 250° C. and the detector temperature was 270° C. A sample stream split ratio of 40 to 50:1 was used It is clear from these results that, under the influence of the transesterification catalyst, the methyl esters of the $C_{12}$, $C_{14}$, $C_{16}$ and $C_{18}$ fatty acids are smoothly converted to wax esters. It should be noted, however, that the gas chromatographic technique employed, although resolving the wax esters in total carbon number order, did not enable good resolution between wax esters containing the same number of carbon atoms. For example, the resolution achieved between a $C_{12}$-$C_{16}$ wax ester and a $C_{14}$-$C_{14}$ wax ester was relatively poor.

EXAMPLE 2

665 grams of crude fatty alcohol product which had been subjected to transesterification under the conditions outlined in Example 1 were distilled under vacuum in a simple laboratory distillation unit, the boiler of which was fitted with a short packed column to prevent droplet entrainment. The dimensions of the packed column were 2.5 cm diameter×30 cm high, packed with 4 mm Raschig rings. The results are summarised in Tables 3 and 4 below. The analysis figures of Table 4 are again expressed as % w/w The abbreviations used in Table 4 are the same as these used in Table 2.

TABLE 3

| Fraction | Fore run | Product | Residue |
|---|---|---|---|
| Pressure (bar) | 0.014 | 0.013 | 0.013 |
| Temperature | up to 141° C. | 141–170° C. | Not distilled |
| Weight (g) | 96.1 | 537.1 | 30.0 |

TABLE 4

| Fraction | ANALYSIS | | |
|---|---|---|---|
| | Fore run | Product | Residue |
| Methanol | trace | — | — |
| Unknown 1 | 0.86 | — | — |
| $C_{12}$ Alkane | 1.22 | 0.04 | — |
| Unknown 2 | 1.53 | — | — |
| $C_{14}$ Alkane | 1.35 | 0.21 | — |
| Unknown 3 | 0.91 | — | — |
| Unknown 4 | 0.17 | — | — |
| $C_{16}$ Alkane | 0.47 | 0.33 | — |
| Unknown 5 | 2.36 | — | — |
| Unknown 6 | 0.46 | — | — |
| $C_{12}$ Me Ester + $C_{18}$ Alkane | 0.03 | 0.01 | 0.01 |
| Unknown 7–10 | 0.60 | 0.40 | 0.04 |
| $C_{12}$ Alcohol | 75.34 | 59.66 | 0.30 |
| $C_{14}$ Me Ester | trace | — | — |
| Unknown 11–12 | 0.11 | 0.2 | — |
| $C_{14}$ Alcohol | 10.24 | 29.51 | 1.50 |
| $C_{16}$ Me Ester | 0.03 | — | — |
| Unknown 13 | trace | trace | trace |
| Unknown 14–15 | 0.01 | — | — |
| $C_{16}$ Alcohol | 3.16 | 8.91 | 6.86 |
| $C_{18}$ Me Ester | 0.09 | — | — |
| $C_{18}$ Alcohol | 0.29 | 0.06 | 0.88 |
| Wax Esters: | | | |
| $C_{12}$—$C_{12}$ | 0.02 | — | 0.37 |
| Other wax esters | 0.28 | 0.8 | 81.66 |
| Other unknowns | 0.09 | — | 8.36 |

Because the transesterification catalyst remained active throughout the distillation and because the lower alcohols were progressively removed from the system by the distillation procedure, the wax esters remaining in the distillation residue were of higher molecular weight than in the starting material In other words there was continuous ester interchange amongst the wax esters during distillation with a progressive loss of the more volatile fatty alcohol components to the distillate.

EXAMPLE 3

The distillation residue of Tables 3 and 4 was divided into two portions One portion was heated to 180° C. for 2 hours with methanol at a methanol:wax ester mole ratio of 20:1 and the other portion was heated at the same temperature and for the same time but at a methanol:wax ester ratio of 40:1. Upon quench cooling, analyses in % w/w were obtained, using the gas chromatographic technique of Example 2, as set out in Table 5 below The abbreviations in Table 5 are the same as are used in Tables 2 and 4. The analytical figures are expressed on a methanol free basis.

TABLE 5

| Portion No. | 1 | 2 |
|---|---|---|
| $C_{12}$ Me ester | 32.94 | 34.56 |
| $C_{12}$ Alcohol | 0.17 | 0.13 |
| $C_{14}$ Me ester | 4.48 | 4.88 |
| $C_{14}$ Alcohol | 2.54 | 2.43 |
| $C_{16}$ Me ester | 0.56 | 0.62 |
| $C_{16}$ Alcohol | 41.27 | 42.75 |
| $C_{18}$ Me ester | 0.33 | trace |
| $C_{18}$ Alcohol | 7.85 | 8.16 |
| Wax esters | | |
| (a) $C_{12}$—$C_{12}$ | 0.02 | trace |
| (b) $C_{12}$–$C_{14}$ | 0.27 | 0.33 |
| (c) $C_{12}$–$C_{16}$ | 7.04 | 5.17 |
| (d) $C_{14}$—$C_{14}$ | 2.52 | 0.98 |

It can be seen from these results that, in comparison with the composition of the residue of Table 4, treatment with methanol has effected a considerable conversion of the wax esters to $C_{12}$, $C_{14}$, $C_{16}$ and $C_{18}$ fatty alcohols and to the methyl esters of $C_{12}$, $C_{14}$, $C_{16}$ and $C_{18}$ fatty acids. This conversion has, moreover, been effected without the addition of further alkyl titanate transesterification catalyst, thus demonstrating that the transesterification catalytic activity has survived the vacuum distillation step of Example 2.

We claim:

1. A process for the recovery of fatty alcohol or alcohols from a fatty alcohol fraction containing a major molar amount of at least one fatty alcohol and a minor molar amount of at least one lower alkyl fatty acid ester, which process comprises:
   (a) subjecting the fatty alcohol fraction to transesterification in the presence of a transesterification catalyst in a first transesterification zone maintained under transesterification conditions, thereby to convert substantially all of any lower alkyl fatty acid ester present in the feed mixture by ester interchange with a corresponding amount of fatty alcohol or alcohols to lower alkanol and to a wax ester derived from a fatty alcohol and a fatty acid;
   (b) separating resulting lower alkanol from the reaction mixture of step (a) by vaporisation to yield an intermediate transesterification product mixture that is at least partially free from lower alkanol and contains a fatty alcohol or alcohols and a wax ester or esters;
   (c) distilling fatty alcohol or fatty alcohols and wax ester or wax esters of the intermediate transesterification product mixture of step (b) to yield (i) an overhead fraction that contains the fatty alcohol or alcohols and is substantially free from lower alkyl fatty acid ester, and (ii) a distillation residue comprising fatty alcohol or alcohols, and wax ester or esters;
   (d) subjecting the distillation residue of step (c) to transesterification in the presence of added lower alkanol and of a transesterification catalyst in a second transesterification zone maintained under transesterification conditions, thereby to reconvert wax ester or esters to lower alkyl fatty acid ester or esters and to fatty alcohol or alcohols;
   (e) evaporating unreacted lower alkanol from the reaction mixture of step (d) to yield a liquid residue that is substantially free from lower alkanol; and
   (f) distilling fatty alcohol or alcohols and lower alkyl fatty acid ester or esters of the liquid residue of step (e) to produce (i) an overhead product containing a mixture of a lower alkyl fatty acid ester or esters and fatty alcohol or alcohols and (ii) a relatively involatile residue.

2. A process for the production of fatty alcohol which comprises hydrogenating a lower alkyl fatty acid ester or esters in a hydrogenation zone containing a charge of a hydrogenation catalyst and maintained under hydrogenation conditions to yield a mixture of (i) lower alkanol and (ii) a fatty alcohol fraction containing a fatty alcohol or alcohols and a minor amount of unreacted lower alkyl fatty acid ester or esters; and which further comprises:
   (a) subjecting the fatty alcohol fraction to transesterification in the presence of a transesterification catalyst in a first transesterification zone maintained under transesterification conditions, thereby to convert substantially all of any lower alkyl fatty acid ester present in the feed mixture by ester interchange with a corresponding amount of fatty alcohol or alcohols to lower alkanol and to a wax ester derived from a fatty alcohol and a fatty acid;
   (b) separating resulting lower alkanol from the reaction mixture of step (a) by vaporisation to yield an intermediate transesterification product mixture that is at least partially free from lower alkanol and contains a fatty alcohol or alcohols and a wax ester or esters;
   (c) distilling fatty alcohol or fatty alcohols and wax ester or wax esters of the intermediate transesterification product mixture of step (b) to yield (i) an overhead fraction that contains the fatty alcohol or alcohols and is substantially free from lower alkyl fatty acid ester and (ii) a distillation residue comprising fatty alcohol or alcohols, and wax ester or esters;
   (d) subjecting the distillation residue of step (c) to transesterification in the presence of added lower alkanol and of a transesterification catalyst in a second transesterification zone maintained under transesterification conditions, thereby to reconvert wax ester or esters to lower alkyl fatty acid ester or esters and to fatty alcohol or alcohols;
   (e) evaporating unreacted lower alkanol from the reaction mixture of step (d) to yield a liquid residue that is substantially free from lower alkanol;
   (f) distilling fatty alcohol or alcohols and lower alkyl fatty acid ester or esters of the liquid residue of step (e) to produce (i) an overhead product containing a mixture of a lower alkyl fatty acid ester or esters and fatty alcohol or alcohols and (ii) a relatively involatile residue; and
   (g) recycling material of the overhead product of step (f) to the hydrogenation step.

3. A process according to claim 1 or claim 2, in which the transesterification catalyst of step (a) is an alkyl titanate.

4. A process according to any one of claims 1 or 2, in which the transesterification catalyst of step (d) is an alkyl titanate.

5. A process according to any one of claims 1 or 2, in which the transesterification catalyst of step (a) is an alkyl titanate and in which the intermediate transesterification product of step (b) is distilled in step (c) without prior separation of the transesterification catalyst therefrom.

6. A process according to any one of claims 1 or 2, in which the transesterification catalyst of step (d) is an alkyl titanate and in which the liquid residue of step (e) is distilled in step (f) without prior separation of the transesterification catalyst therefrom.

7. A process according to any one of claims 1 or 2, in which at least a part of the relatively involatile residue of step (f) is recycled to step (c) to provide transesterification catalyst for use in the first transesterification zone.

8. A process according to claim 1 or 2, in which the transesterification catalyst of step (a) is an alkali metal alkoxide.

9. A process according to claim 1, or claim 2 in which the transesterification catalyst of step (d) is an alkali metal alkoxide.

10. A process according to claim 8 in which the intermediate transesterification product mixture of step (b) is passed through a bed of an acidic ion exchange resin containing —$SO_3H$ and/or —COOH groups to neutralise the alkali metal alkoxide prior to the distillation step (c).

11. A process according to claim 9, in which the liquid residue of step (e) is passed through a bed of an acidic ion exchange resin containing —SO$_3$H and/or —COOH groups to neutralise the alkali metal hydroxide prior to the distillation step (f).

12. A process according to claim 1 or claim 2, in which the lower alkyl ester or esters is or are methyl esters and in which the lower alkanol is methanol.

* * * * *

UNITED STATES PATENT AND TRADEMARK OFFICE
CERTIFICATE OF CORRECTION

PATENT NO. : 5,138,106

DATED : August 11, 1992

INVENTOR(S) : Martyn Wilmott et al.

It is certified that error appears in the above-identified patent and that said Letters Patent is hereby corrected as shown below:

Col. 1, line 53 "triglycerides" should be --triglycerides.--

Col. 3, line 45 "production" should be --Production--.

Col. 5, line 45 "1tetradecanol" should be --1-tetradecanol--.

Col. 6, line 31 "bar" should be --bar.--.

Col. 6, line 56 "used" should be --used.--.

Col. 8, line 2 "alkoxids" should be --alkoxide--.

Col. 8, line 44 "drawings" should be --drawings,--.

Col. 8, line 53 "item," should be --items--.

Col. 9, line 4 "methanol" should be --methanol.--.

Col. 10, line 16 "quantity" should be --quantity.--.

Col. 12, line 29 "catalyst" should be --catalyst.--.

Col. 12, line 34 "0 99" should be --0.99--.

Col. 12, line 36 "Products)" should be --Products, p.l.c.)--.

UNITED STATES PATENT AND TRADEMARK OFFICE
CERTIFICATE OF CORRECTION

PATENT NO. : 5,138,106
DATED : August 11, 1992
INVENTOR(S) : Martyn Wilmott et al.

It is certified that error appears in the above-identified patent and that said Letters Patent is hereby corrected as shown below:

Col. 12, line 37 "isopropyl/butyl" should be --iso-propyl/n-butyl--.

Col. 12, line 46 "Me" should be --$C_{18}$Me--.

Col. 13, line 29 "bar" should be --bar.--.

Col. 13, line 37 "used" should be --used.--.

Col. 13, line 59 "w/w" should be --w/w.--.

Col. 14, line 6 (table 4, col. 2, line 2) "0.86" should be --0.84--.

Col. 14, line 34 "material" should be --material.--.

Col. 14, line 42 "portionsOne" should be --portions. One--.

Col. 16, line 59 (claim 8) "or 2" should be --or claim 2--.

Signed and Sealed this

Fifth Day of October, 1993

BRUCE LEHMAN

Attest:

*Attesting Officer*    Commissioner of Patents and Trademarks